(12) United States Patent
Joschek et al.

(10) Patent No.: US 8,227,626 B2
(45) Date of Patent: Jul. 24, 2012

(54) PREPARATION OF FLUORINATED 1,3-BENZODIOXANES

(75) Inventors: Jens Peter Joschek, Cologne (DE); Albrecht Marhold, Leverkusen (DE); Axel Pleschke, Cologne (DE)

(73) Assignee: LANXESS Deutschland GmbH, Leverkusen (DE)

( * ) Notice: Subject to any disclaimer, the term of this patent is extended or adjusted under 35 U.S.C. 154(b) by 0 days.

(21) Appl. No.: 13/008,296

(22) Filed: Jan. 18, 2011

(65) Prior Publication Data
US 2011/0112313 A1    May 12, 2011

Related U.S. Application Data

(63) Continuation of application No. 11/201,412, filed on Aug. 10, 2005, now abandoned.

(30) Foreign Application Priority Data

Aug. 17, 2004 (DE) .......................... 10 2004 039 876

(51) Int. Cl.
*C07D 319/08* (2006.01)
(52) U.S. Cl. ..................................................... 549/365
(58) Field of Classification Search .................... 549/365
See application file for complete search history.

(56) References Cited

U.S. PATENT DOCUMENTS 3,632,820 A    1/1972    Alles et al.

*Primary Examiner* — David K O Dell
(74) *Attorney, Agent, or Firm* — Michael A. Miller

(57) ABSTRACT

The invention relates to novel fluorinated achiral 1,3-benzodioxanes of the general formula (I-a) and (I-b)

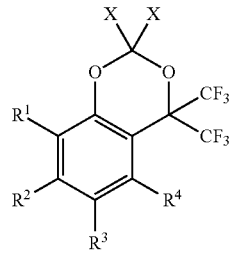

(I-a)

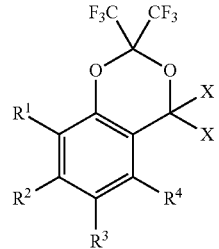

(I-b)

and to the preparation thereof.

11 Claims, No Drawings

PREPARATION OF FLUORINATED 1,3-BENZODIOXANES

This application is a continuation of Ser. No. 11/201,412 filed Aug. 10, 2005, incorporated herein by reference.

The invention relates to novel fluorinated achiral 1,3-benzodioxanes and to the preparation thereof.

Fluorinated 1,3-benzodioxanes, especially the corresponding aminobenzodioxanes, are valuable intermediates for the synthesis of life science active ingredients, especially of active pharmaceutical ingredients in cancer therapy.

In the field of the fluorinated 1,3-benzodioxanes, the only compounds known to date have either borne two different substituents on one of the methylene carbons and/or not had sufficient lipophilicity for use as building blocks for active pharmaceutical ingredients (DE-A 16 43 382). In the case of the compounds which have a stereocentre, a costly and inconvenient enantiomer separation before further use is required.

There is therefore a need to circumvent the problem of enantiomer separation, which cannot be solved satisfactorily with the current state of the art, and to provide fluorinated 1,3-benzodioxanes suitable for further processing to give active pharmaceutical ingredients.

The object on which the present invention is based is thus to provide suitable fluorinated 1,3-benzodioxanes for which no costly and inconvenient enantiomer separation is required and which are suitable, for example, for further processing to give active pharmaceutical ingredients for cancer therapy.

It has been possible, surprisingly, using a new synthesis strategy, to circumvent the chirality problem by introducing a second identical substituent on the methylene group, and to noticeably increase the lipophilicity in the active ingredient molecules. With few synthetic steps, a multitude of compounds of the general formulae (I-a) or (I-b) can be obtained.

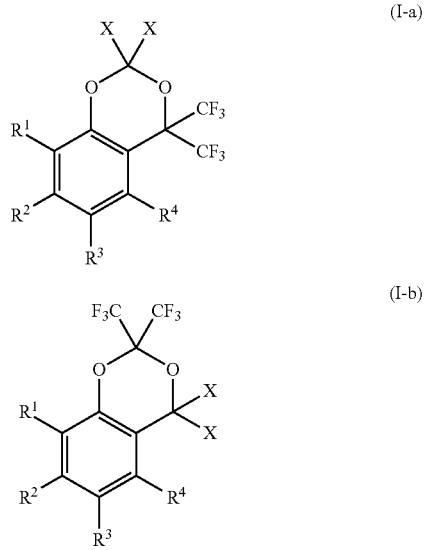

The present invention therefore provides compounds of the general formulae (I-a) or (I-b)

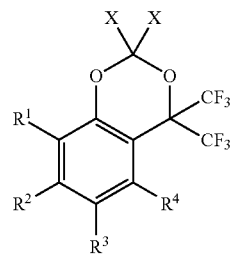

(I-a)

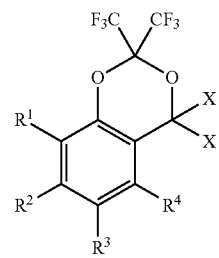

(I-b)

where $R^1$, $R^2$, $R^3$, $R^4$ are each independently H, CN, $NO_2$, $NH_2$, OH, halogen, linear or branched, optionally partly fluorinated or perfluorinated $C_1$-$C_4$-alkyl radicals, linear or branched, optionally partly fluorinated or perfluorinated $C_1$-$C_4$-alkoxy radicals, CHO, COOH, COOR, $SO_2CH_3$, $SO_2$Hal, optionally substituted phenyl or pyridyl radicals, fluorocarbonyl, benzoyl, trifluoroacetyl, phenoxy, isocyanato, $SO_2F$ and difluorochloromethyl radicals, where R is a $C_1$-$C_4$-alkyl radical and Hal is a halogen radical, X is H, Cl or F, preferably F.

$R^1$, $R^2$, $R^3$ and $R^4$ are each independently H, CN, $NO_2$, $NH_2$, Br, $CH_3$, $CF_3$, $OCH_3$, $OCF_3$, CHO, COOH, COOR or $SO_2CH_3$, where R is preferably a $C_1$-$C_4$-alkyl radical.

In preferred embodiments of the present invention, at least one of the $R^1$, $R^2$, $R^3$ and $R^4$ radicals is different to H.

In further preferred embodiments of the present invention, at least one of the $R^1$, $R^2$, $R^3$ and $R^4$ radicals is independently CN, $NO_2$, $NH_2$, Br, CHO, COOH, COOR or $SO_2CH_3$, preferably $NO_2$ or $NH_2$, where R is a $C_1$-$C_4$-alkyl radical, and all further $R^1$, $R^2$, $R^3$ and $R^4$ radicals are each independently H, $CH_3$, $OCH_3$, $OCF_3$ or $CF_3$.

Unless specifically stated otherwise, $C_1$-$C_4$-alkyl and $C_1$-$C_4$-alkoxy in the context of the invention are preferably each independently a straight-chain, cyclic, branched or unbranched alkyl and alkoxy radical respectively, which may optionally be further substituted.

For example, $C_1$-$C_4$-alkyl is more preferably methyl, ethyl, n-propyl, isopropyl, n-butyl or tert-butyl.

For example, $C_1$-$C_4$-alkoxy is preferably methoxy, ethoxy, isopropoxy, n-propoxy, n-butoxy or tert-butoxy.

Unless specifically stated otherwise, halogen, in the context of the invention is fluorine, chlorine, bromine or iodine. For example, halogen is preferably fluorine, chlorine or bromine, more preferably fluorine or chlorine.

Exemplary compounds of the inventive 1,3-benzodioxanes are the following:

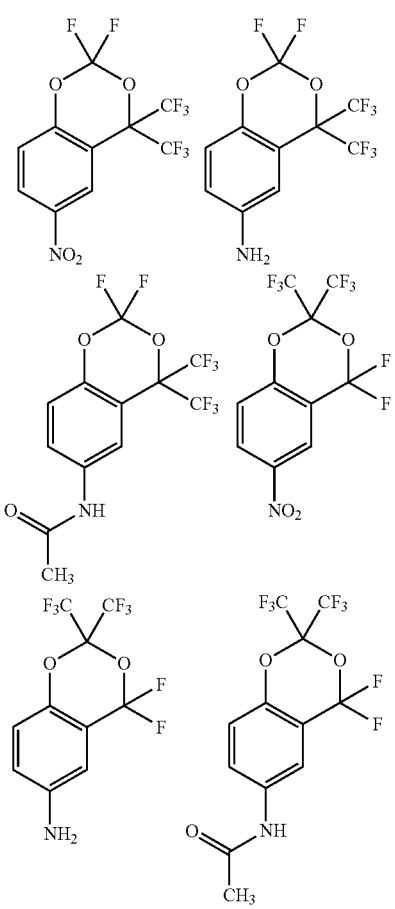

Unlike most known compounds, the inventive compounds of the general formula (I-a) or (I-b) are achiral, so that the problem of enantiomer separation does not occur in their preparation. The inventive compounds can therefore be prepared in a simpler manner than the known chiral compounds.

Compounds of the general formula (I-a) may begin, for example, with reaction of a phenol with hexafluoroacetone to give the ketal, followed by a ring-building reaction with dihalomethanes, formaldehyde or other $C_1$ units. Subsequent chlorination on the methylene group and subsequent fluorination lead to the inventive compound which can then optionally be subjected to further substitutions on the aromatic ring. Further reactions of the substituents on the aromatic ring, for example oxidations, reductions, esterifications or amidations, etc., are also possible.

The present invention therefore further provides a process for preparing an inventive compound, wherein
  a) a dihydroxy compound of the general formula (II-a)

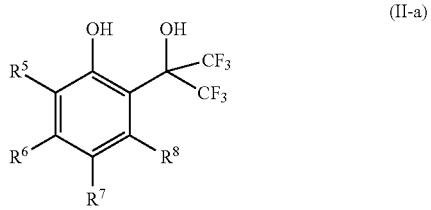

(II-a)

where
  $R^5$, $R^6$, $R^7$, $R^8$ are each as defined for $R^1$, $R^2$, $R^3$ and $R^4$
  and
  is reacted with an optionally substituted dihalomethane, formaldehyde or another $C_1$ unit,
  b) optionally chlorinated subsequently on the methylene group, and
  c) subsequently fluorinated on the methylene group.

As already detailed, the ketals of the general formula (I) may be prepared, for example, by reacting a phenol with hexafluoroacetone.

Compounds of the general formula (I-b) may be prepared, for example, starting from hydroxy- or halobenzyls which bear a hydroxyl group or a halogen in the ortho-position, with the reaction with hexafluoroacetone and subsequent ring-closure reaction with acids or under Buchwald conditions, i.e., for example, with palladium(dibenzylideneacetone) and tris(tert-butyl)phosphine as a catalyst in boiling toluene and sodium tert-butoxide as a base. The further derivatization via chlorination and chlorine-fluorine exchange is effected analogously to the preparation of the compounds of the general formula (I-a).

The chlorination may be effected, for example, with a series of chlorinating agents, for example chlorine, $PCl_3$, $PCl_5$ and combinations thereof. However, preference is given to effecting the chlorination with chlorine, more preferably under irradiation with an Hg vapour lamp. The chlorination is effected in substance or in at least one solvent, at at least one temperature of ±30° C. above and below the boiling point of the substance or of any solvent(s) used.

The solvents used are preferably those which are inert towards the chlorinating agent(s), especially towards chlorine, under the conditions of the chlorination. These are, for example, halogenated solvents, for example chlorobenzotrifluoride, dichlorobenzotrifluoride.

The fluorination may be effected by means of a series of fluorinating agents, for example HF, alkali metal and transition metal fluorides and main groups element fluorides, for example KF or $SbF_3$, or else ammonium fluorides of the $R_4N^+F^-$ type, where R is $C_1$-$C_4$-alkyl. However, preference is given to effecting the fluorination with anhydrous HF. Preference is further given to carrying out the fluorination at a temperature of, for example, −10° C. to 20° C., more preferably with an excess of anhydrous HF.

The variations mentioned of substituents and functional groups in the aromatic ring of the benzodioxane system may be achieved by three different strategies. One is to provide the phenol reactant with different substituents which remain unchanged on the molecule throughout the entire synthesis and can later if appropriate be converted to further derivatives. In order to be able to ensure regioselectivity in the case of unsymmetric starting compounds, it is sensible in some cases to introduce reversible protecting groups in the ortho-position before the reaction with hexafluoroacetone. A further possibility available for achieving a particular substitution pattern on the aromatic ring is that of electrophilic aromatic substitution on the finished fluorinated 1,3-benzodioxane system, for example a nitration, from which a further derivatization, for example via reduction to the amino group and subsequent conversion to the amide, is possible. A third possibility is the nucleophilic attack on the finished fluorinated 1,3-benzodioxane systems, for example with lithium alkyls and the subsequent classic derivatization of the organometallic compounds.

The present invention therefore further provides a process for preparing the inventive compounds, wherein a substitution on the aromatic ring and/or a reaction on at least one of any substituents present on the aromatic ring is carried out either after above-described fluorination or in another stage of the above-described process for preparing the inventive compounds.

The present invention further provides a process for preparing an inventive compound, wherein a compound of the general formula (I-a) or (I-b) is substituted on the aromatic ring and/or a reaction is carried out on at least one of any substituents present on the aromatic ring.

The inventive compounds are outstandingly suitable for use as intermediates or building blocks in active pharmaceutical ingredients, especially for cancer therapy.

EXAMPLES

Example 1 a) Preparation of 2-[2,2,2-trifluoro-1-hydroxy-1-(trifluoromethyl)ethyl]phenol

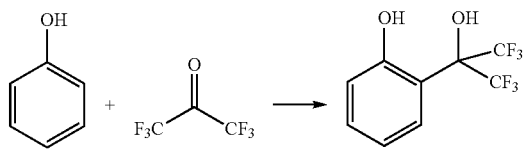

94.11 g (1000 mmol) of phenol and 166.02 g (100 mmol) of $AlCl_3$ were initially charged in 1200 ml of 1,2-dichloroethane and cooled to −35° C. At this temperature, the precalculated amount of 166.02 g (1000 mmol) of hexafluoroacetone was metered in from a bomb. Subsequently, the reaction mixture was allowed to come to room temperature (20° C., RT) and stirred at RT for a further 36 h. The reaction flask was subsequently flushed with $N_2$ and the offgas passed into a wash bottle containing water. For workup of the remaining reaction solution, 500 ml of water were added cautiously and the mixture was stirred well. Subsequently, the organic phase was removed, the aqueous phase was extracted with $CH_2Cl_2$ and dried over magnesium sulphate, and the solvent was removed on a rotary evaporator. As this was done, the residue crystallized out. For purification, the resulting crystals were slurried in n-hexane and filtered off, and 230 g (842 mmol, yield: 82.4% of theory) of a white, crystalline solid were obtained.

b) Preparation of 4,4-bis(trifluoromethyl)-4H-1,3-benzodioxane

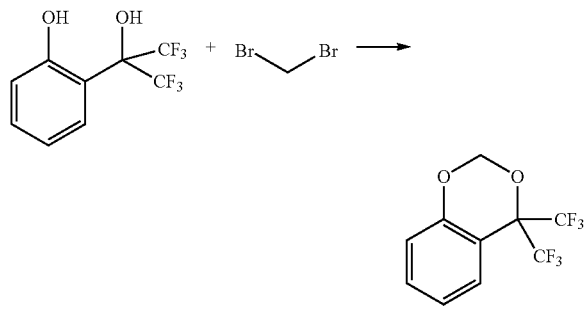

100.00 g (380 mmol) of the product from example 1a) and 111.67 g (1920 mmol) of potassium fluoride were initially charged in 1200 ml of dry N,N-dimethylformamide (DMF) and heated to 130° C. Over 75 min, 73.51 g (420 mmol) of dibromomethane were metered in and the mixture was stirred for a further 2 h. GC monitoring was used to detect full conversion. After cooling to RT, the reaction mixture was admixed with 3 l of dist. $H_2O$. Subsequently, the mixture was divided and extracted in each case with 3×300 ml of methyl tert-butyl ether (MTBE), the organic phases were combined, washed 1× with 100 ml of 1 M aqueous NaOH, washed 2× with 1 l of dist. $H_2O$ and dried over magnesium sulphate, and the solvent was removed on a rotary evaporator. A red liquid was obtained. After distillation through a horizontal condenser at 6.7 mbar and a top temperature of 68° C., 57 g (205 mmol, yield: 52.86% of theory at a purity of 98%) of the product distilled over as a clear liquid.

c) Preparation of 2,2-dichloro-4,4-bis(trifluoromethyl)-4H-1,3-benzodioxane by chlorination of 4,4-bis(trifluoromethyl)-4H-1,3-benzodioxane

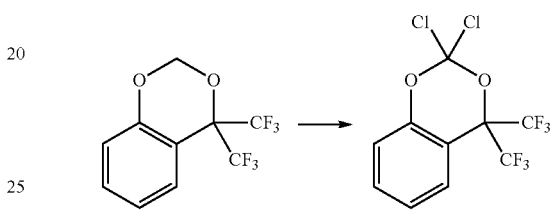

57 g (205 mmol) of the product from example 1b) were initially charged, 5 g (37 mmol) of $PCl_3$ were added and chlorine was introduced at 165° C. for 6 hours under irradiation of a Hg vapour lamp. At 5.6-5 mbar, a bath temperature of 130° C. and a top temperature of 80-85° C., the dichlorine compound was distilled over a small horizontal condenser. Yield: 34 g (99.7 mmol), 41.77% of theory at a purity of 86%) of colourless liquid d) Preparation of 2,2-difluoro-4,4-bis(trifluoromethyl)-4H-1,3-benzodioxane by fluorination of 2,2-dichloro-4,4-bis(trifluoromethyl)-4H-1,3-benzodioxane

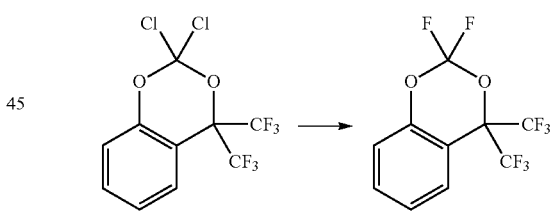

150 ml of anhydrous HF were initially charged at −4° C. and 34 g (99.70 mmol) of product from example 1c) were added dropwise at −5° C. depending on the HCl evolution. On abatement of gas evolution, the temperature was allowed to rise to RT and the mixture was stirred for a further 4 h. Subsequently, the reaction mixture was added to a mixture of 350 g of ice and 650 g of $CH_2Cl_2$. The aqueous and the organic phase were separated from one another, the aqueous phase was re-extracted 1× with 200 ml of $CH_2Cl_2$, the organic phases were dried over magnesium sulphate, and the solvent was removed on a rotary evaporator. 2,2-Difluoro-4,4-bis(trifluoromethyl)-4H-1,3-benzodioxane was obtained in 95% purity in a yield of 17 g (52% of theory).

e) Preparation of 2,2-difluoro-4,4-bis(trifluoromethyl)-4H-1,3-(6-nitrobenzo)dioxane by nitration of 2,2-difluoro-4,4-bis(trifluoromethyl)-4H-1,3-benzodioxane

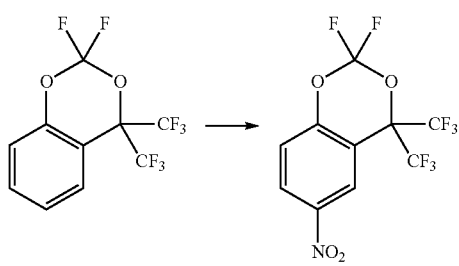

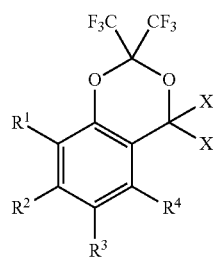

7.9 ml of $H_2SO_4$ were initially charged and 6.5 ml of $HNO_3$ were added dropwise with cooling. At 10° C., 17 g of the product from example 1d) were added dropwise within 5 minutes and the mixture was stirred for a further 10 minutes, in the course of which the nitrated target product precipitated out. The reaction mixture was added to 400 ml of ice, extracted 3× with 80 ml each time of ethyl acetate, washed 3× with 10% $NaHCO_3$ and dried over magnesium sulphate, and the solvent was removed. Yield: 18 g of yellow solid (95% of theory)

f) Preparation of 2,2-difluoro-4,4-bis(trifluoromethyl)-4H-1,3-(6-aminobenzo)dioxane

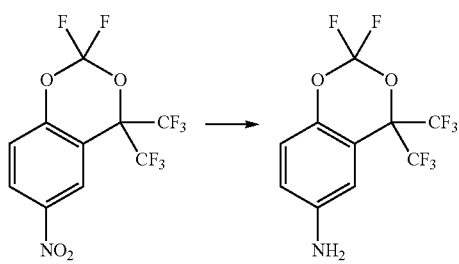

18 g of the product from example 1e) were initially charged in 250 ml of acetic acid and 6.4 g of iron were metered in at reflux temperature (internal temperature 105° C.) within 2 hours. The reaction mixture was subsequently poured onto 500 ml of ice, extracted 3 × with 300 ml of ethyl acetate, dried over magnesium sulphate and freed of solvent. The crude product was distilled over a small horizontal condenser. The target product distilled over at 0.1 mbar and a bath temperature of 90-110° C. 2,2-Difluoro-4,4-bis(trifluoromethyl)-4H-1,3-(6-aminobenzo)dioxane was obtained with a yield of 60% of theory.

The invention claimed is:

1. A process for preparing a compound according to the general formula (I-a) or (I-b),

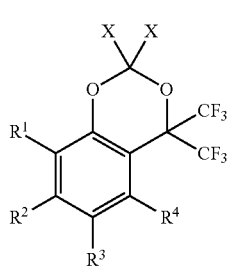
(I-a)

-continued

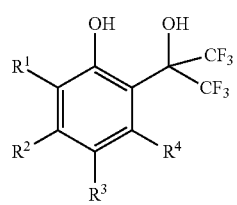
(I-b)

where $R^1$, $R^2$, $R^3$, $R^4$ are each independently H, CN, $NO_2$, $NH_2$, Br, $CH_3$, $CF_3$, $OCH_3$, $OCF_3$, CHO, COOH, COOR, $NHCOCH_3$, or $SO_2CH_3$, where R is a $C_1$-$C_4$-alkylene, and X is H, Cl or F, comprising:

reacting a dihydroxy compound of the general formula (II-a)

(II-a)

where $R^5$, $R^6$, $R^7$, $R^8$ are each as defined above, with an optionally substituted dihalomethane or formaldehyde; and optionally, chlorinating a methylene group, and/or fluorinating a methylene group.

2. The process according to claim 1, wherein the fluorination is effected using anhydrous HF.

3. The process according to claim 1, wherein the fluorination is effected a temperature of from −10° C. to 20° C.

4. The process according to claim 1, wherein $R^5$, $R^6$, $R^7$ and $R^8$ are each H.

5. A compound of the general formula (I-a) or (I-b),

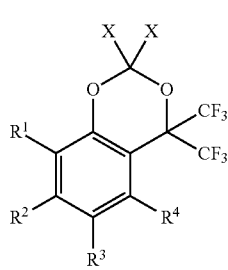
(I-a)

-continued

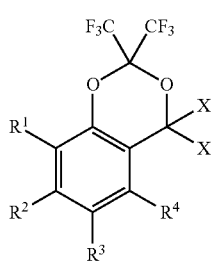
(I-b)

where

R¹, R², R³, R⁴ are each independently H, CN, NO$_2$, NH$_2$, Br, CH$_3$, CF$_3$, OCH$_3$, OCF$_3$, CHO, COOH, COOR, NHCOCH$_3$, or SO$_2$CH$_3$, where R is a C$_1$-C$_4$-alkylene, and X is H, Cl or F.

6. The compound (I-a) or (I-b) of claim 5, wherein X is F.

7. The compound (I-a) or (I-b) of claim 5, wherein at least one of R¹, R², R³ and R⁴ is not H.

8. The compound (I-a) or (I-b) of claim 5, wherein at least one of R¹, R², R³ and R⁴ is CN, NO$_2$, NH$_2$, Br, CHO, COOH, COOR, NHCOCH$_3$ or SO$_2$CH$_3$, where R is a C$_1$-C$_4$-alkylene, and all further R¹, R², R³ and R⁴ are independently H, CH$_3$, OCH$_3$, OCF$_3$ or CF$_3$.

9. The compound (I-a) or (I-b) of claim 5, wherein:
R¹, R² and R⁴ are H; and
R³ is H, NO$_2$, or NH$_2$.

10. The compound (I-a) or (I-b) of claim 5, wherein the compound (I-a) or (I-b) is selected from the group consisting of:

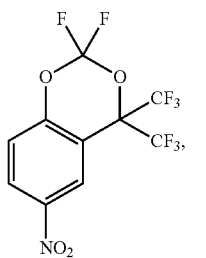 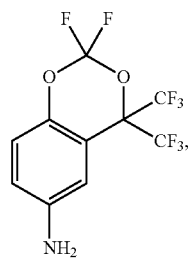

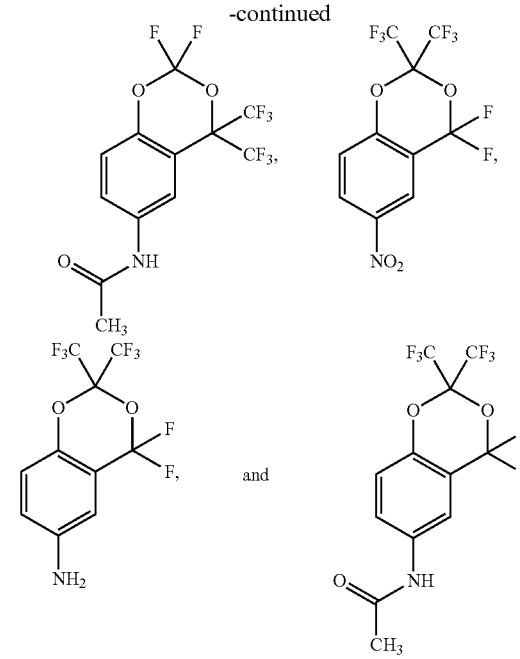

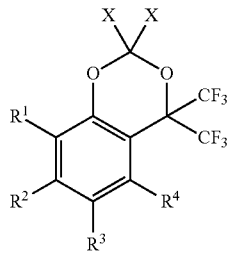

11. A compound of formula I-a, (I-a)

wherein:
R¹, R² and R⁴ are H;
R³ is H, NO$_2$, or NH$_2$; and
X is H, Cl or F.

* * * * *